(12) United States Patent
Stampfer

(10) Patent No.: US 6,245,021 B1
(45) Date of Patent: Jun. 12, 2001

(54) METHOD FOR DIAGNOSING PSYCHIATRIC DISORDERS

(75) Inventor: Hans George Stampfer, Darlington (AU)

(73) Assignee: HeartLink NA Patent Corporation, Bridgetown (BB)

(*) Notice: Subject to any disclaimer, the term of this patent is extended or adjusted under 35 U.S.C. 154(b) by 0 days.

(21) Appl. No.: 09/402,869
(22) PCT Filed: Apr. 14, 1998
(86) PCT No.: PCT/AU98/00252
§ 371 Date: Jan. 27, 2000
§ 102(e) Date: Jan. 27, 2000
(87) PCT Pub. No.: WO98/46128
PCT Pub. Date: Oct. 22, 1998

(30) Foreign Application Priority Data

Apr. 11, 1997 (AU) .................................................. PO 6166

(51) Int. Cl.[7] ....................................................... A61B 5/02
(52) U.S. Cl. ........................... 600/481; 600/509; 607/45; 128/898
(58) Field of Search ..................................... 600/481–500, 600/544; 128/898–899; 607/45

(56) References Cited

U.S. PATENT DOCUMENTS

| | | |
|---|---|---|
| 4,753,246 | 6/1988 | Freeman . |
| 4,779,100 | 10/1988 | Voelz . |
| 4,800,893 | 1/1989 | Ross et al. . |
| 4,896,675 | 1/1990 | Ohsuga et al. . |
| 5,280,793 | 1/1994 | Rosenfeld . |
| 5,577,510 | 11/1996 | Chittum et al. . |
| 5,871,517 | * | 2/1999 | Abrams et al. .................. 607/45 |

FOREIGN PATENT DOCUMENTS

| | | |
|---|---|---|
| 504945 | 9/1992 | (EP) . |
| 2501996 | 9/1982 | (FR) . |
| 2185815 | 7/1987 | (GB) . |

OTHER PUBLICATIONS

Derwent Abstract Accession No. 98–123990/12, class SO5, JP 10–005201 A (Nissan Motor Co Ltd) Jan. 13, 1998.

* cited by examiner

Primary Examiner—John P. Lacyk
Assistant Examiner—Ryan Carter
(74) Attorney, Agent, or Firm—Kohn & Associates

(57) ABSTRACT

A method for diagnosing a psychiatric disorder in a subject, the method comprising the steps of measuring the pattern of a subject's heart rate, and using said pattern to diagnose the psychiatric disorder. Also disclosed is a method for assessing the effectiveness of a treatment for a psychiatric disorder, comprising measuring a heart rate pattern of a subject before treatment, measuring a heart rate pattern of the subject during treatment, and comparing the patterns for changes to determine the effectiveness of the treatment.

23 Claims, 9 Drawing Sheets

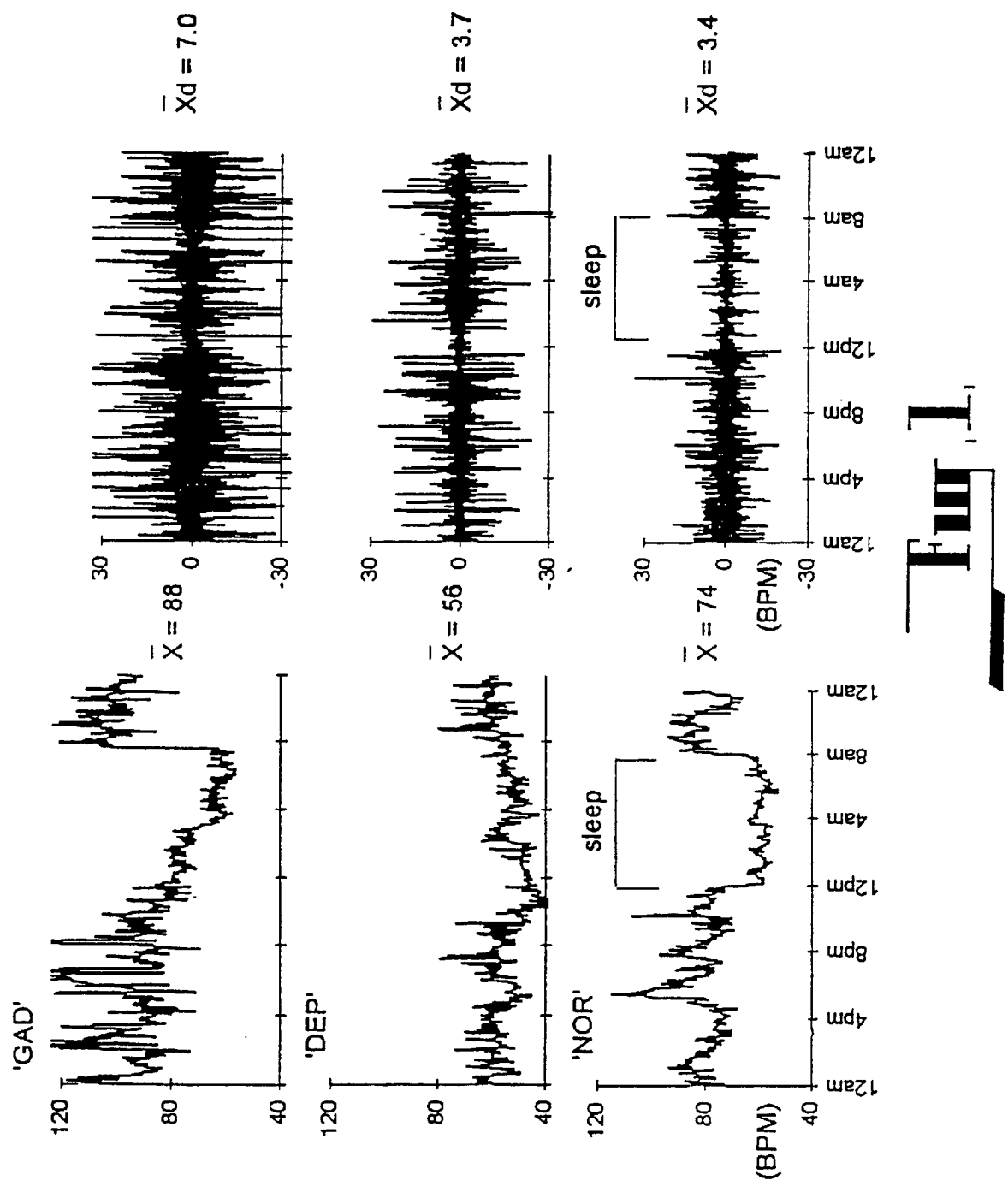

Figures 2A, 2B:
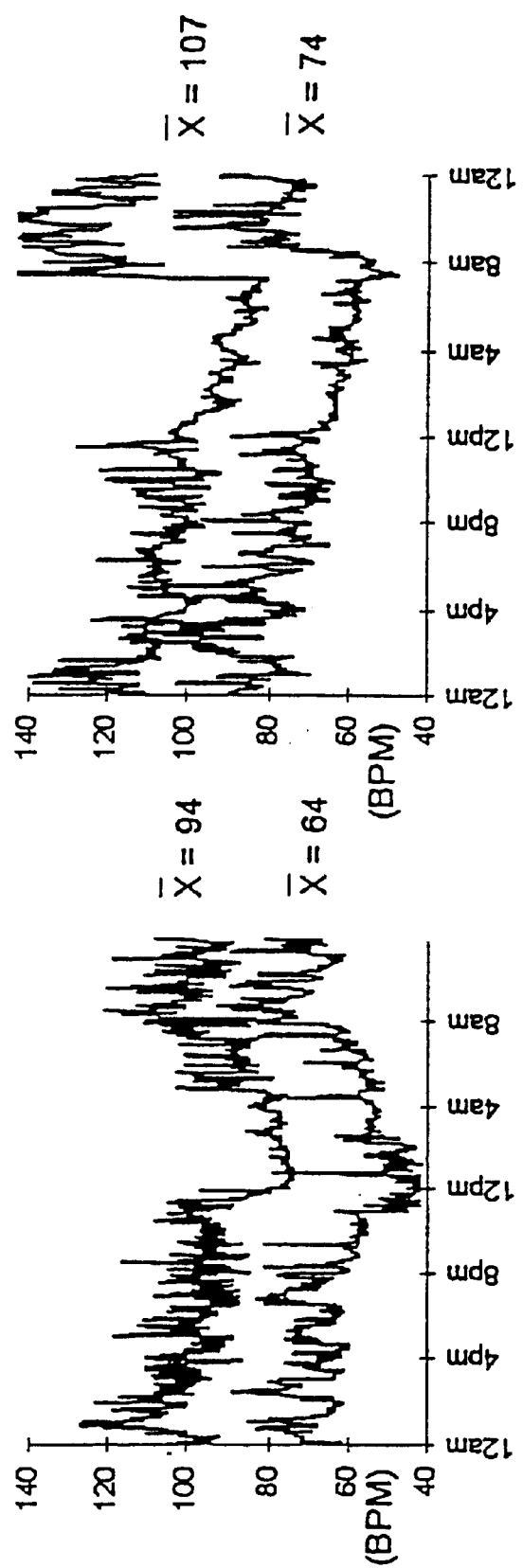

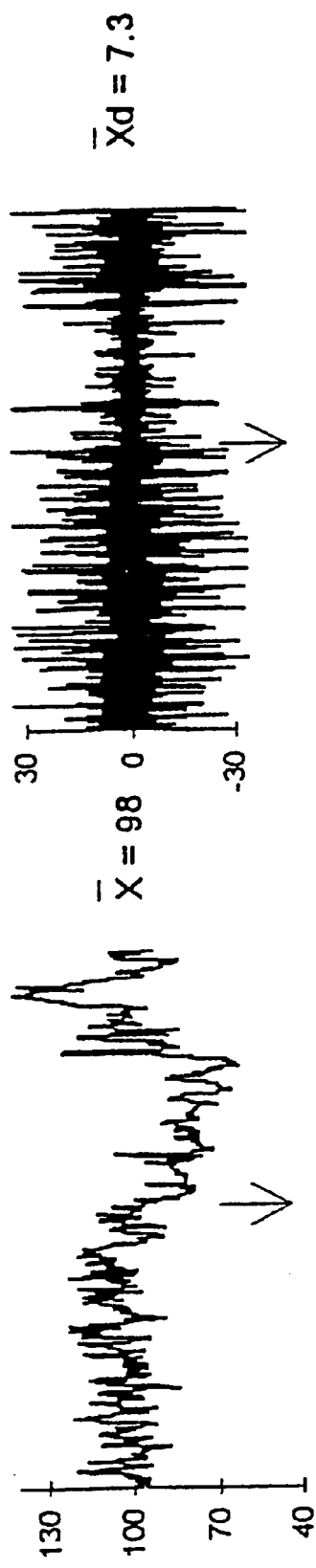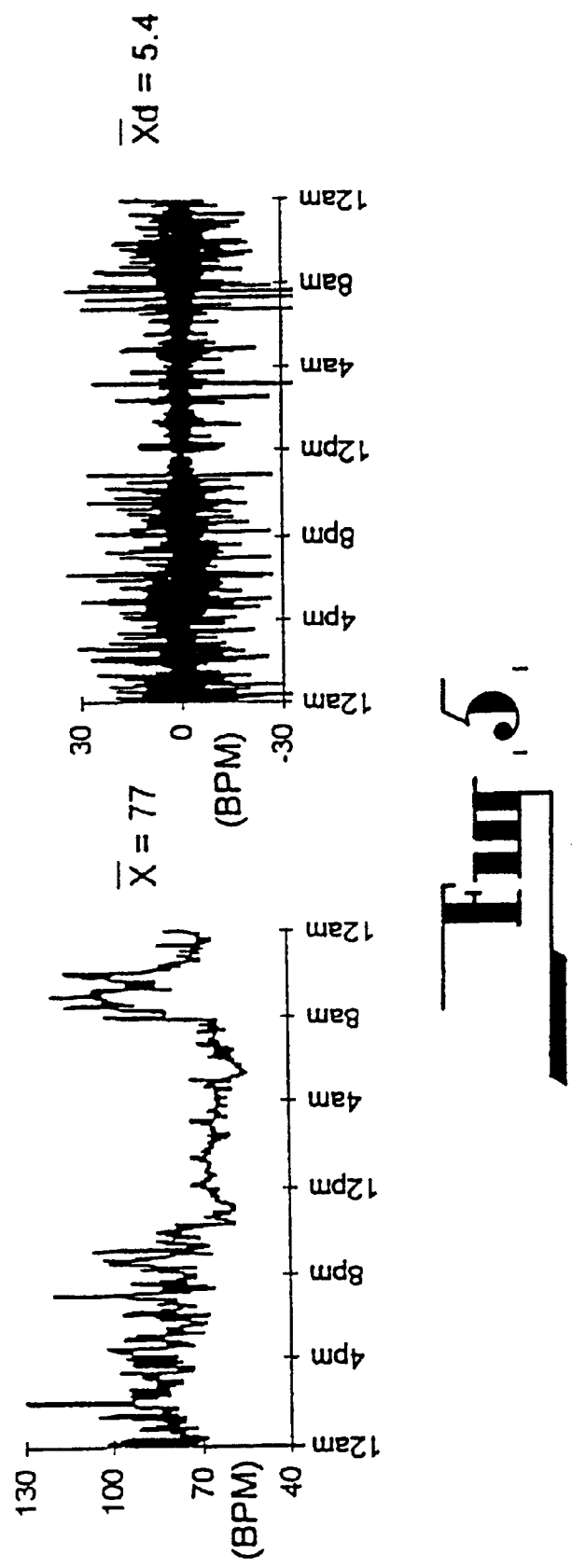
Fig. 5

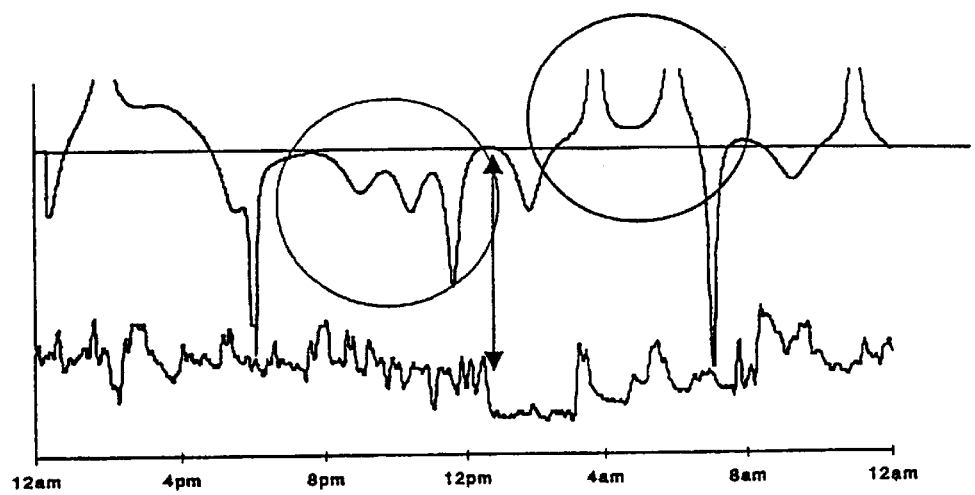
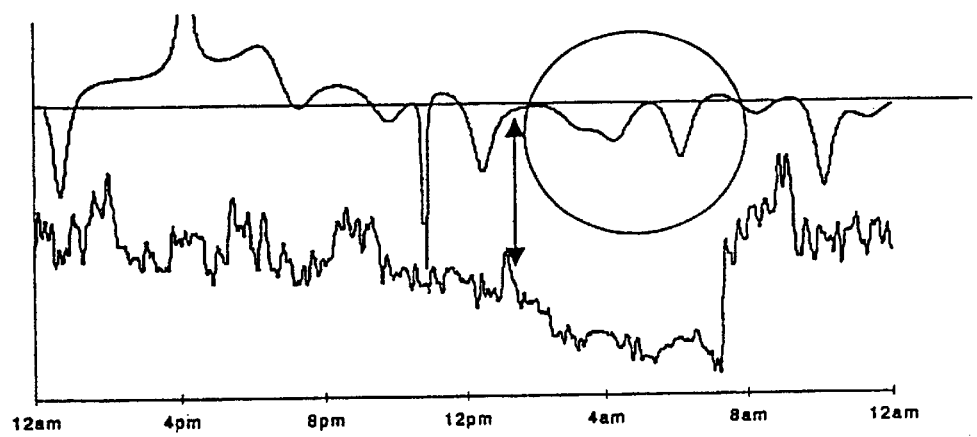
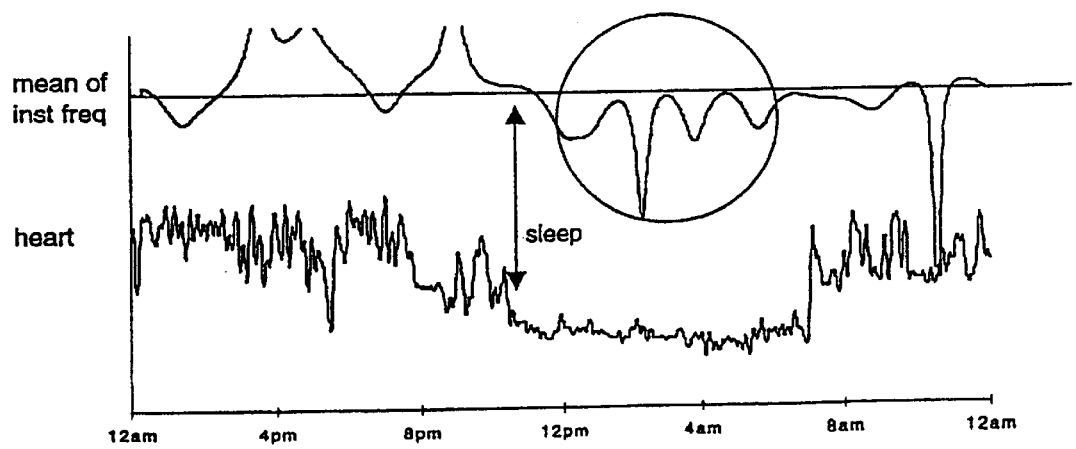
Fig. 8.

METHOD FOR DIAGNOSING PSYCHIATRIC DISORDERS

BACKGROUND

The present invention relates to a method for diagnosing psychiatric disorders by monitoring the pattern of a subject's heart rate, and more particularly to a method for diagnosing psychiatric disorders by monitoring at least a portion of a subject's circadian heart rate pattern. The present invention also provides a method for assessing the effectiveness of treatments for psychiatric disorders.

Despite intensive research for nearly a century, there is still no reliable 'laboratory test' for mental illness. Diagnoses are still made 'clinically', on the basis of subjective experience [symptoms] and observed behaviour [signs]. Given the difficulties of defining normal experience and behaviour and the lack of any reliable objective indicators, it is not surprising that to date, all systems of diagnosis/classification in psychiatry have been less than satisfactory for one reason or another. A reliable laboratory test would be of enormous practical value in everyday clinical practice and contribute greatly to advancement in theory and practice more generally.

It is suggested that hitherto attempts to find 'laboratory indicators' of mental illness have failed because of their conceptually misguided approach. Previous researchers have tended to look for some 'fixed' chemical/anatomical lesion in the brain, in imitation of a neurological or neuropathological approach. If, however, there is no such 'fixed' lesion, but rather a functional disregulation, [like a 'tuning problem' in a car and TV set], then the neuropathological approach is doomed to failure.

The present invention seeks to provide a method for diagnosing psychiatric disorders or to at least provide a diagnostic method that may provide objective indications of clinical status and change and contribute to the diagnostic assessment of a subject.

SUMMARY OF THE INVENTION

The present invention provides a method for diagnosing a psychiatric disorder in a subject, the method comprising the steps of: measuring the subject's heart rate pattern and; using said pattern to diagnose the psychiatric disorder.

The present invention is based on the identification of a psychophysiological correlation between heart rate and psychiatric status. In this respect, it has been found that certain clinical states are consistently associated with distinctly different heart rate patterns.

The heart rate pattern may be measured over a variety of time periods. Thus, in one form the heart rate pattern is a circadian heart rate pattern, in that it is measured over a 24 hour period. Whilst the entire circadian heart rate pattern may be used in the method of the present invention, certain portions of the circadian heart rate pattern may also be used to diagnose psychiatric disorders. In this respect, psychiatric disorders may be identified and diagnosed from analysis of characteristic patterns within portions of the circadian heart rate pattern.

Thus, the present invention also provides a method for diagnosing a psychiatric disorder in a subject, the method comprising the steps of: measuring at least a portion of the subject's circadian heart rate pattern and; using said pattern or portion thereof to diagnose the psychiatric disorder.

When the method comprises the measurement a portion of the circadian heart rate pattern the portion measured may be varied provided the portion is capable of exhibiting a pattern that correlates to a psychiatric disorder. In one particular form, the heart rate pattern is measured over a period of at least approximately 90 minutes.

The heart rate pattern of a subject whilst asleep and during the transition from being awake to asleep and asleep to awake may be particularly useful in the method of the present invention. Thus, when the method comprises the measurement a portion of the circadian heart rate pattern, the portion of the circadian heart rate pattern is preferably the sleep portion and in particular the sleep portion including the transition of the subject into and out of sleep.

The heart rate pattern may be measured in a variety of formats. Preferably, the heart rate pattern is measured as beats per minute over time. Alternatively, the heart rate pattern may be measured as a difference plot which reflects variations or fluctuations in heart rate. When the heart rate pattern is a difference plot, the difference plot is preferably a plot of [heart rate (t+1)–heart rate (t)], where t is time in minutes, over time.

Of course, the heart rate pattern of a subject may be measured in a plurality of formats and the plurality of formats may be used together to diagnose psychiatric disorders according to the method of the present invention. Thus, the present invention also provides a method for diagnosing a psychiatric disorder in a subject, the method comprising the steps of: measuring the subject's heart rate pattern in a plurality of formats, such as beats per minute over time and [heart rate (t+1)–heart rate (t)], where t is time in minutes, over time and; diagnosing the psychiatric disorder.

The method of the present invention may be computerised. In this respect, a subject's heart rate pattern may be measured and recorded in a form that allows it to be cross-checked with a database of reference heart rate patterns indicative of psychiatric disorders.

Thus, the present invention also provides a method for diagnosing a psychiatric disorder in a subject, the method comprising the steps of: measuring the heart rate pattern of the subject and; comparing said pattern with at least one reference heart rate pattern indicative of a psychiatric disorder wherein the reference heart pattern is provided in a computerised database.

The subjects heart rate pattern may be measured in a variety of ways. Preferably, the subjects heart rate is measured with a monitor that is unobtrusive and leaves the person freely ambulant.

When the method of the present invention involves the use of reference heart rate patterns, the reference heart rate patterns may be varied and preferably are developed by collecting data from a sufficient number of patients with psychiatric disorders to determine a typical pattern.

When the biophysical parameter is a circadian heart rate pattern, the reference heart rate pattern may be selected from those illustrated in the examples and in particular those patterns illustrated in FIGS. 1 to 4.

The present invention may be used to diagnose a variety of psychiatric disorders. For example, the method of the present invention may be used to diagnose a psychiatric disorder selected from the group comprising; General Anxiety Disorder (GAD), Panic Disorder (PD), Obsessive-Compulsive Disorder (OCD), non-psychotic Major Depression, Somatoform Disorder (hypochondriacal type), Delusional Disorder (paranoid and somatic type) Attention Deficit Disorder (ADD) and acute Schizophreniform Disorder.

Heart rate patterns may be affected by a range of factors. Some factors may produce noise that may hamper the interpretation of the heart rate pattern, which is clearly undesirable. To assist in accounting for and thus negating the effects of noise, the method of the present invention may further comprise the recordal of a subject's activities throughout the time the subject is being subjected to the method.

Thus, the present invention provides a method for the diagnosis of a psychiatric disorder in a subject, the method comprising the steps of: measuring the subject's heart rate pattern; comparing the subject's heart rate pattern with a record of the subject's activities and; comparing said pattern with at least one reference heart rate pattern indicative of a psychiatric disorder wherein the comparison of the subject's heart rate pattern with the record of the subjects activities allows for the effects of noise in the subject's heart rate pattern to be negated.

Preferably, the record of the subject's activities comprises a daily diary that is completed by the subject when being subjected to the method of the present invention.

The present invention may also be useful for monitoring the effectiveness of a particular treatment administered to a subject suffering from a psychiatric disorder.

Thus, the present invention also provides a method for assessing the effectiveness of a treatment for a psychiatric disorder, the method comprising the steps of: measuring the subject's heart rate pattern before and during said treatment and; comparing said patterns for changes to determine the effectiveness of the treatment. In one particular form, the subject heart rate pattern may be measured before, during and after said treatment to assess the efficacy of the treatment.

Preferably, the treatment is a drug treatment in which the drug is administered to the subject. For example, the drug treatment may involve the administration of a drug selected from the group comprising; benzodiazepines; antidepressants such as Selective Serotonin Reuptake Inhibitors (SSRI's), Tri-cyclic Antidepressants (TCA's) and Reversible Inhibitor of Monoamines (RIMA's); and sertraline.

The present invention will now be described with reference to the following examples. The description of the examples in no way limits the generality of the preceding description.

EXAMPLES

The data presented in examples 1 and 2 illustrate the relationship between circadian pattern of heart rate and psychiatric disorders. The independent variable in the examples was an ACTIVE axis I DSM-IIIR disorder ("IIIR"—revised third edition of the diagnostic manual published by the American Psychiatric Association); the dependent variable, 24MAHR. Efforts were made to control for a number of possible confounding influences on heart rate. All subjects were given careful instructions in diary keeping. The diary consisted of a single card with provision for hourly ratings of potentially confounding influences that included: physical exertion, intake of tea/coffee/alcohol/nicotine and social interaction.

Only certain diagnoses were studied. The aim was to select readily diagnosed states between normality and psychosis and the following were included; Generalized Anxiety Disorder (GAD), Panic Disorder, Obsessive-Compulsive Disorder (OCD), non-psychotic Major Depression, Somatoform Disorder (hypochondriacal type), Delusional Disorder (paranoid and somatic type) and acute Schizophreniform Disorder.

Clinical subjects were selected from consecutive admissions to an adult psychiatric unit of a large teaching hospital. Normal control subjects (without any history of psychiatric illness) were obtained from students, nursing, clerical and medical staff. Patients were included in the study initially if they satisfied DSM-IIIR criteria for one of the above listed axis I disorders. Age was restricted to 18–65. Subjects were required to be physically healthy and were excluded, if after full physical examination and relevant laboratory investigations, there was evidence of any physical disorder that might affect heart rate. Subjects were also excluded if there was any evidence of recent alcohol and illicit drug abuse.

Whilst efforts were made to select subjects who had not taken any medications within two weeks of admission, those who had been taking medications were not excluded if at the time of recording, they showed clear evidence of an active axis I disorder included in the study. Medication histories were recorded in all cases and the inclusion of both medication free subjects with those who had been or were taking medication at the time of recording, gave the opportunity to examine medication effects in each diagnostic category.

Measures of 24 hour, minute average heart rate (24MAHR) were obtained with the use of a heart monitor that returned data comparable to that obtained using a conventional ECG monitor. Data acquisition was unobtrusive and left the person freely ambulant.

The number of serial recordings per subject ranged from 2–10, with a rounded mean of 3 per subject. The purpose of taking serial recordings, was to examine the extent of intra-subject variation in circadian activity, depending upon changes in mental state. Typically, serial recordings were obtained every third day. Diagnostic reassessment was undertaken prior to each serial recording. As data were obtained over more than two years, it was possible to obtain serial recordings over relatively long periods in a percentage of subjects who were readmitted during this period.

Whilst plots of heart rate v's time of day can reveal the qualitative aspect of circadian activity at a glance, it is difficult to quantify this temporal aspect in a numerical form and there are certain difficulties in creating composite group data. There are a number of pitfalls in simply averaging the data. There are obvious changes in heart rate depending on whether a person is awake or asleep (see FIG. 1) and there is considerable variation in the sleep habits of different individuals—both in terms of when they go to sleep and the length of time they usually sleep. Hence, if one were to simply average group data, the resulting average would inevitably be confounded by overlapping segments of sleep/awake activity between subjects. Also, potentially relevant transient changes, such as a sudden elevation or reduction in heart rate during sleep and awake periods, would tend to become degraded or 'lost' with averaging. Hence averaging is not an appropriate method of group data reduction for comparing patterns of circadian activity between different diagnoses.

A comparison of the qualitative aspect requires a pattern classification of individual recordings in terms of particular 'morphological' features. This was the approach taken in the examples. Individual records of 24MAHR were superimposed on a VDU and classified into different pattern types, based on their circadian morphology. A frequency count was then made, of the pattern types found in each diagnosis and a Chi-square test applied to see if any particular pattern predominated.

Findings are presented below; Example 1 describes qualitatively different circadian patterns and illustrates how these data can provide clinically useful information. Example 2 shows the results of group data analysis and includes an analysis of medication effects.

Example 1

Measures of 24MAHR provide a time history of two broadly different, but complementary, aspects of circadian activity. The first aspect, which is clearly evident in time plots of the raw data, consists of the broad contours of activity that are created by changes in the baseline mean around which minute pulse rates vary. The second aspect is revealed in a variability or difference plot, [pulse rate (t+1)–pulse rate (t), with t in minutes], and consists of the changing trends in minute pulse variation that are to some extent independent of the broad mean contours. These two complementary aspects are illustrated in FIG. 1, which shows typical examples of three broadly different circadian patterns. The patterns illustrated in FIG. 1 were found commonly in subjects with General Anxiety Disorder (GAD), non-psychotic Depression (DEP) and normal subjects (NOR).

Plots of the corresponding first differential, are shown on the right. The respective 24 hour scalar means [$\overline{X}$] and [$\overline{X}d$], in beats per minute (BPM), are shown at the end of each plot. The plots on the left show visibly obvious differences in the broad circadian pattern or architecture, particularly in the pattern of activity extending over the sleep period. The sleep period is most clearly defined in normal data. There is a rapid decline in heart rate at the onset of sleep, an equally rapid rise on waking and a relatively flat pattern of low rate activity in between. By comparison, GAD data, show a well defined, large elevation of heart rate on waking, but no rapid decline to mark the onset of sleep. Instead, there is a progressive decline from awake rates to the lowest rates, just before waking. The opposite occurs in subjects suffering from Depression (DEP). Typically in these subjects the onset of sleep is marked by a relatively rapid decline in heart rate, that is followed by a fluctuating, but progressive elevation towards awake levels, without a clearly defined transition from sleep to waking. In GAD, heart rates are relatively high at the onset of sleep and at their lowest just before waking. In DEP it is the reverse.

Turning to the first differential plots on the right of FIG. 1, it can be seen that normal data show the lowest differential mean of 3.4 BPM and the highest value of 7.0 BPM occurs in GAD. However, it should be noted that the 24 hour mean ($\overline{X}$) is not a reliable indicator of the amount or pattern of minute pulse variation. That is, the changes in minute pulse variation are to some extent independent of the broad contours of activity.

More generally, it can be seen that these differential plots also reveal something of a circadian pattern, which is created by variation in the amount of activity at different times of the day. Again, this architecture of circadian variation is most clearly defined in normal data, which show a clear reduction in pulse variation at the onset of sleep, followed by a visibly reduced level of activity during the sleep interval and a return to pre-sleep levels on waking. By comparison, Depression shows only a brief period of reduced activity at the onset of sleep, followed by a rapid return to pre-sleep activity, even while the mean trend is still below the pre-sleep awake values. GAD data show a discernible reduction in sleep activity similar to what is evident in normal data, but the reduction is less obvious and there is a much greater amount of activity during the sleep interval.

More generally, and compared to normal, the data for GAD and Depression show more spiking throughout the 24 hour period. The differences in activity extending over the sleep period, in both the broad mean contours and amount of minute pulse variation, are regarded as particularly significant, in that one would expect the least number of confounding influences during sleep. The evident differences over this period are likely to be particularly valid indicators of genuine physiological differences between these states. Apart from qualitative differences, the data in FIG. 1 also show quantitative differences in the 24 hour means indicated at the end of each plot.

FIGS. 2a and 2b, show further typical patterns associated with Depression (FIG. 2a) and GAD (FIG. 2b) and their corresponding 24 hour means. It can be seen that typical GAD and DEP patterns can extend over a range of baseline offsets and whilst the 24 hour mean is usually found to be lower in Depression than GAD, FIGS. 2a and 2b show that this is not always the case. It can be seen that the 24 hour mean of 94 BPM for the top plot in FIG. 2a is significantly higher than the 24 hour mean of 76 BPM for the bottom plot in FIG. 2b. This shows that the qualitative differences between these two patterns, cannot be explained simply by quantitative differences in the 24 hour mean. This does not mean that quantitative differences within and between particular patterns are irrelevant and the significance of such quantitative variation is discussed in more detail below in Example 2.

Although states of GAD and Depression will most commonly reveal the respective signature patterns of circadian activity as shown in FIGS. 1 and 2, individual recordings may show a number of minor variations that provide potentially useful information about particular individuals. For example, a typical GAD pattern might show the following variations while still retaining its signature contour.

There may be variation in baseline offset as shown in FIG. 2. There may be variation in the gradient of declining activity during the sleep interval, as well as the gradient and relative elevation of heart rate on waking. There may be variation in the pattern of insomnia, as indicated by the amount of spiking activity to waking levels during the sleep interval. There may be a greater or lesser amount of minute pulse variation throughout the 24 hours or selected intervals of time. Hence, just as two individuals with an undoubted clinical diagnosis of GAD for example, may show some variation in the severity and number of clinical phenomena, so may the 24 hour pattern show some variation, but still retain it's signature GAD contour.

However, subjects may also exhibit mixed heart rate patterns, with features of both GAD and DEP, that seem analogous to mixed mental state phenomena one finds in the clinical domain. These mixed patterns suggest a dynamic continuum of manifestations and the circadian pattern in individual cases may depend on the relative amount of activation in two broadly different physiological pathways. In this sense, it may be that the typical patterns for GAD and Depression shown in FIGS. 1 and 2, reflect 'pure' GAD and 'pure' Depression respectively, whereas mixed forms reflect activation of both GAD and Depression physiology. An example of such a mixed pattern ('MIX') is shown in FIG. 3 together with a GAD and a Depression pattern.

Such patterns were found less commonly in subjects diagnosed as Panic Disorder, GAD and Depression, and it is emphasised in this regard, that these subjects were not given a mixed diagnosis on clinical assessment. However, their heart rate showed a circadian pattern that appears to fall between the more common typical patterns for GAD and Depression.

Figure 3:
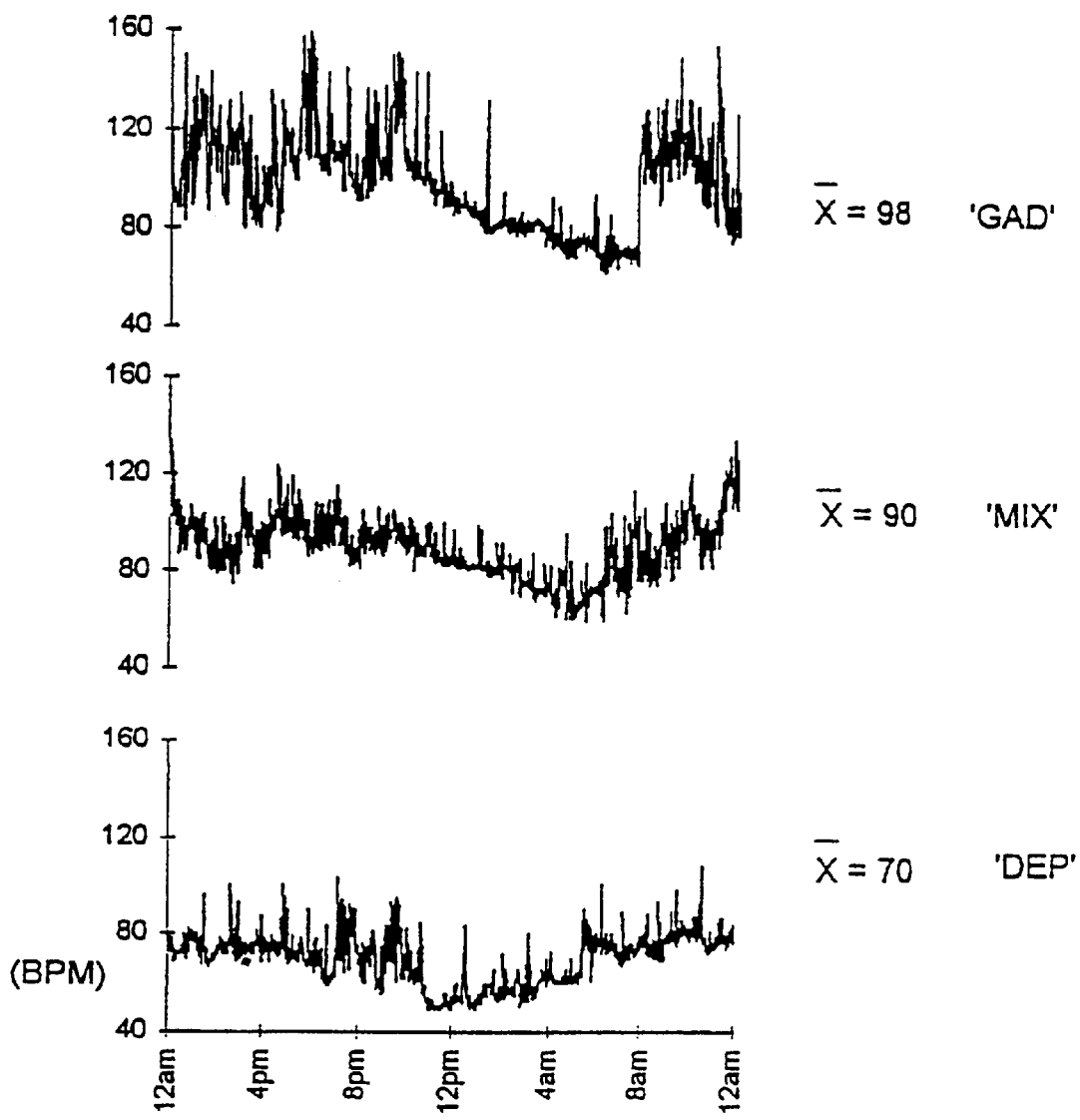

The mixed pattern in FIG. 3 has been placed between further examples of typical GAD and DEP patterns, to facilitate an appreciation of what is meant by mixed. It can be seen that the mixed pattern shows a progressive decline of activity into the sleep period that closely resembles the GAD pattern above it. However, the similarity ends at around 4:00 am. Thereafter there is a progressive increase in heart rate to awake levels, that resembles the Depression pattern immediately below. This suggests a combined activation of GAD and Depression physiology and even if this interpretation requires modification, the physiological perspective revealed by these data may contribute practically useful adjunct information in a variety of clinical and research applications.

In all, seven broadly different circadian patterns were identified and practically all the data obtained, could be broadly classified into one or other of these patterns. Four of these seven patterns, namely, Normal, GAD, Depression and Mixed, have already been presented above. The remaining three, shown in FIG. 4, have been found to be most common in patients with Panic Disorder (PAN), Obsessive-Compulsive Disorder or Delusional Disorder (HSR) and acute Schizophreniform Psychosis (SCH).

The PAN pattern is characterized by a flat pattern of activity for much of the 24 hour period, a relatively low 24 hour mean and a relatively large amount of spiking pulse variation. There is a discernible flat sleep period (from around midnight to 8 am), defined by a small baseline shift down and a slight reduction in the amount of minute pulse variation.

The HSR pattern resembles the normal pattern but differs in the consistently high rates of flat activity both in the awake and sleep periods. In the example shown, the sleep interval is clearly defined by a precipitous drop in heart rate at the onset of sleep, an equally precipitous elevation on waking and a relatively flat pattern of activity throughout the sleep period, with rates around 80 BPM. Elevations of sleep rate around and beyond such values, show a progressive disruption of the sleep architecture towards the grossly disorganized pattern which is found in acute schizophreniform states (SCH).

All but two out of all the recordings obtained could be classified broadly into one or other of the seven patterns discussed above. Those which did not conform to one or other of these types, were classified as other (OTH). It is envisaged that further classificatory patterns may be found by including more diagnostic states and by making finer pattern distinctions that include differences in minute pulse variation. Attention has been drawn to minute pulse variation to show how this perspective may also contribute clinically useful information. It was very apparent that the same broad circadian pattern in different individuals, can show considerable variation in the amount and distribution of minute pulse variation.

Serial recordings were obtained from all subjects. However only the first recording from each subject was used for group data comparisons between the different diagnoses included in the study. Subsequent recordings were used to study intra-individual changes and did not contribute to group data. The aim of serial recordings, was to see whether a subject's change in mental state, eg from GAD to normal, was associated with a change in circadian pattern and if so, whether the change recapitulated the most common group data pattern for those states. Such intra-individual state-dependent recapitulation of group data patterns for those states, would give support to the proposed hypothesis of there being a systematic link between psychiatric status and circadian pattern of heart rate.

Example 2

Data presented in Example 2 show that, notwithstanding other influences, patterns of heart rate are demonstrably dependent on mental or psychiatric status. Where mental state alters, for example, from anxious to normal, the pattern of 24 hour activity shows corresponding changes in serial recordings. An example of such state dependent changes is shown in FIG. 5.

The data were obtained from an individual whose symptoms of GAD abated with treatment. Raw data are shown on the left and the corresponding variability data on the right. The respective 24 hour means have been added at the end of each plot. It can be seen that the broad contours of activity change from a typical GAD pattern towards a normal NOR pattern and there are concomitant changes in minute pulse variation. In particular, there is a relative reduction in activity at the onset of sleep and during sleep. From a purely quantitative perspective, there is a reduction in the 24 hour mean ($\bar{X}$) from 98 to 77, and in the differential mean $\bar{X}d$ from 7.3 to 5.4. Taken together, these changes are intuitively consistent with someone becoming less anxious. The advantage of these physiological adjunct data is that they can provide objective indices of clinical change.

It is appropriate at this stage to make some comments about confounding noise. It is well recognised that heart rate is susceptible to a wide range of influences and the data presented here may be contaminated to some extent with noise caused by variation in fitness, age, sex, tea/coffee intake, motor activity, environmental stimulation. etc. Diary keeping can help to control for more obvious influences such as exercise, but a certain amount of noisy contamination will inevitably remain. It is found in this regard that whilst physical exercise and other unusual stimulation/exertion can undoubtedly produce confounding effects, these are readily identified with the help of diary information. Minor and brief influences do not appear to exert a significant confounding effect on the broad contours of activity. Probably this is because such effects are brief and randomly distributed during the waking period. The diagnostically useful information is revealed more in the broad mean trends, which remain distinctly evident despite superimposed high frequency noise. Also, a large number of possible confounding effects do not operate during the sleep period and the pattern of activity during sleep is an important discriminatory feature.

More generally, and excepting unusual effects such as exercise, it appears to be the case that just as similar psychological phenomena (eg symptoms of anxiety and Depression) come to dominate the mental state of normally different individuals, so do mental state dependent patterns of circadian heart rate come to dominate in the physiological domain, despite differences in age, fitness etc. Thus, in the case of GAD for example, it is found that a sport fit 20 year old male and a decidedly unfit 60 year old female will both show a similar GAD pattern, even if there are baseline differences normally.

TABLE 1

| MENTAL STATE | CIRCADIAN PATTERN ||||||||| | |
|---|---|---|---|---|---|---|---|---|---|---|---|
| | NOR | DEP | PAN | GAD | MIX | HIS | SCH | OTH | N | $\bar{X}$ | $\bar{X}d$ |
| Normal | 23 | — | — | 5 | 2 | — | — | — | 30 | 75 | 4.8 |
| Depression | — | 23 | 2 | — | 5 | — | — | — | 30 | 76 | 3.5 |
| Somatoform | 1 | — | 4 | 10 | 6 | 2 | — | 2 | 25 | 82 | 4.1 |
| Panic | — | 1 | 18 | 8 | 3 | — | — | — | 30 | 71 | 5.1 |
| GAD | — | — | — | 24 | 4 | 2 | — | — | 30 | 86 | 4.9 |
| OCD | — | — | — | 5 | 1 | 9 | — | — | 15 | 95 | 4.9 |
| Delusional | — | 1 | — | 8 | 2 | 14 | — | — | 25 | 99 | 4.1 |
| Acute Schizophrenia | — | — | — | 2 | — | 4 | 9 | — | 15 | 107 | 4.9 |

Table 1 shows a summary of group data, in terms of how frequently particular patterns occurred in the different diagnoses. The number of subjects (N), group 24 hour mean ($\bar{X}$) and group 24 hour differential mean ($\bar{X}d$), have been added for each diagnosis. It can be seen that whilst all diagnoses, including normal, are associated with more than one type of circadian pattern, certain diagnoses show a strong association with one particular pattern. If one assumes that the seven identified patterns should be equally distributed in each diagnostic group, then Chi square testing shows a significant predominance (with probabilities>0.05 and 0.001) of a particular pattern in each of the diagnostic groups.

More generally, there are indications of an hierarchical grouping in these correlations. Thus normal subjects showed predominantly a NOR pattern, and of those who did not, all but two showed an anxiety (GAD) pattern. However no normal subject showed an HSR or SCH pattern, which predominate at the psychotic end of the clinical spectrum. Conversely, Delusional and acute Schizophreniform Disorder do not show a NOR pattern. A similar hierarchical grouping is evident for anxiety subtypes of Panic disorder, Generalized Anxiety and Obsessive-Compulsive Disorder. No subject diagnosed as OCD showed a PAN pattern which predominates in Panic Disorder and no subject diagnosed as Panic Disorder showed an HSR pattern which predominates in OCD. However a significant percentage of both Panic Disorder (27%) and OCD (36%) subjects showed a GAD pattern which predominates in Generalized Anxiety Disorder. Whilst larger samples may show a wider overlap, the findings obtained here suggest that statistically, these anxiety subtypes are associated with broadly different circadian patterns, with OCD showing a pattern that predominates at the psychotic end of the clinical spectrum.

Table 1 also shows variation in the 24 hour mean ($\bar{X}$) and 24 hour differential mean ($\bar{X}d$), between the different diagnoses. Taking the mean of 75 BPM for normal subjects as the reference, there are statistically significant elevations with p>0.001 in: GAD, OCD, Delusional Disorder and acute Schizophreniform Disorder. This shows that statistically, some diagnoses reveal circadian activity that differs from normal both qualitatively and quantitatively, whereas in others such as Depression, it differs qualitatively but not quantitatively. However individual recordings of any particular pattern can show quantitative variation in terms of 'baseline offset', as illustrated for DEP and GAD patterns in FIG. 2. The clinical significance of such quantitative variation was not investigated systematically, but in the case of the GAD pattern for example, there is support for the likely explanation that the degree of baseline offset is related to severity.

Table 1 shows that the GAD pattern was found in normal subjects and all diagnoses other than Depression. However the combined 24 hour mean of the GAD pattern in states of Normal, Somatoform and Panic Disorder is significantly lower than it is for states of OCD, Delusional and Acute Schizophreniform Disorder. This indicates that the quantitative aspect is also relevant and it does not seem surprising that in the example of the GAD pattern, the highest means are found at the psychotic end of the clinical spectrum.

It is not known over what range of baseline offset different patterns can exist without undergoing a qualitative change and it may be that any particular pattern depends on the relative contribution and hierarchical progression, of only a few axes of physiological activation (possibly only anxiety and Depression). Thus, both the qualitative and quantitative aspects of circadian heart rate can contribute potentially useful information.

Compared to the raw scalar mean ($\bar{X}$), less difference was found in the differential mean ($\bar{X}d$). However compared to the value of 4.8 BPM for normal subjects, there is a significant reduction (p>0.05) in Depression, Delusional Disorder and Hypochondriacal Somatoform Disorder. Although not significantly different compared to normal subjects, Panic Disorder shows the highest absolute mean of 5.1 BPM whereas Depression shows the lowest absolute mean of 3.6 BPM. The difference in this regard between Panic Disorder and Depression is highly significant with p>0.001.

The ratio of drug free to drug taking subjects varied between diagnoses as did the type of medication. Because of such variation, comparisons were confined to the largest N groups of Depression, GAD and Panic Disorder. The majority of subjects on medication in these three groups, had been or were taking a benzodiazepine at the time of recording and some had also been taking anti-depressants. Surprisingly, no statistically significant differences were found in pattern type or 24 hour means. One might have expected at least a lower 24 hour mean in subjects taking benzodiazepines. Possibly these subjects had a higher heart rates in the first place and whilst medication did have an effect, it did not lower the mean to a significant extent.

The provisional conclusion drawn from these findings is that unless medication is effective in changing mental state, it does not significantly alter the circadian pattern and may not significantly lower the 24 hour mean, even if one does see transient effects, especially with benzodiazepines and sedative major tranquillizers. This is illustrated in FIGS. 6a and 6b, which show transient benzodiazepine effects.

Figure 6:
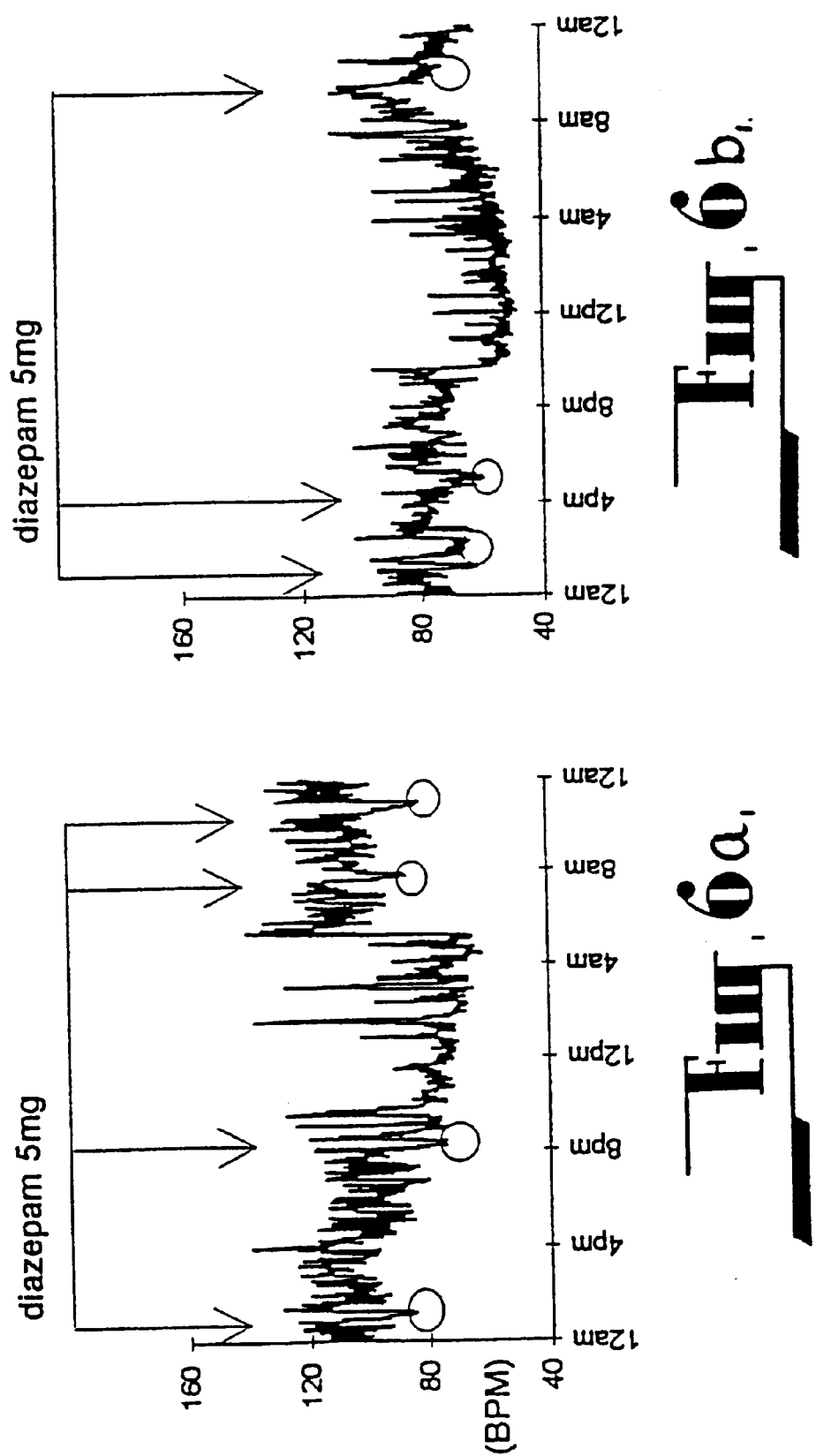

FIG. 6a shows a typical GAD pattern obtained from a subject diagnosed as GAD. FIG. 6b shows a typical DEP pattern from a subject diagnosed as Depression. By chance, both subjects were taking diazepam when the first recording was made. The subject with Depression had been prescribed diazepam initially because of agitation. It can be seen that diazepam resulted in a similar transient lowering of heart rate in both subjects. In neither case do these transient effects apparently alter the broad circadian pattern to any significant extent and the 24 hour mean would have been lowered only minimally by the briefly lower rates. It should be noted that after briefly dropping, the heart rate returns to the pre-medication baseline and even higher rates after some 40 or so minutes.

Figure 4:
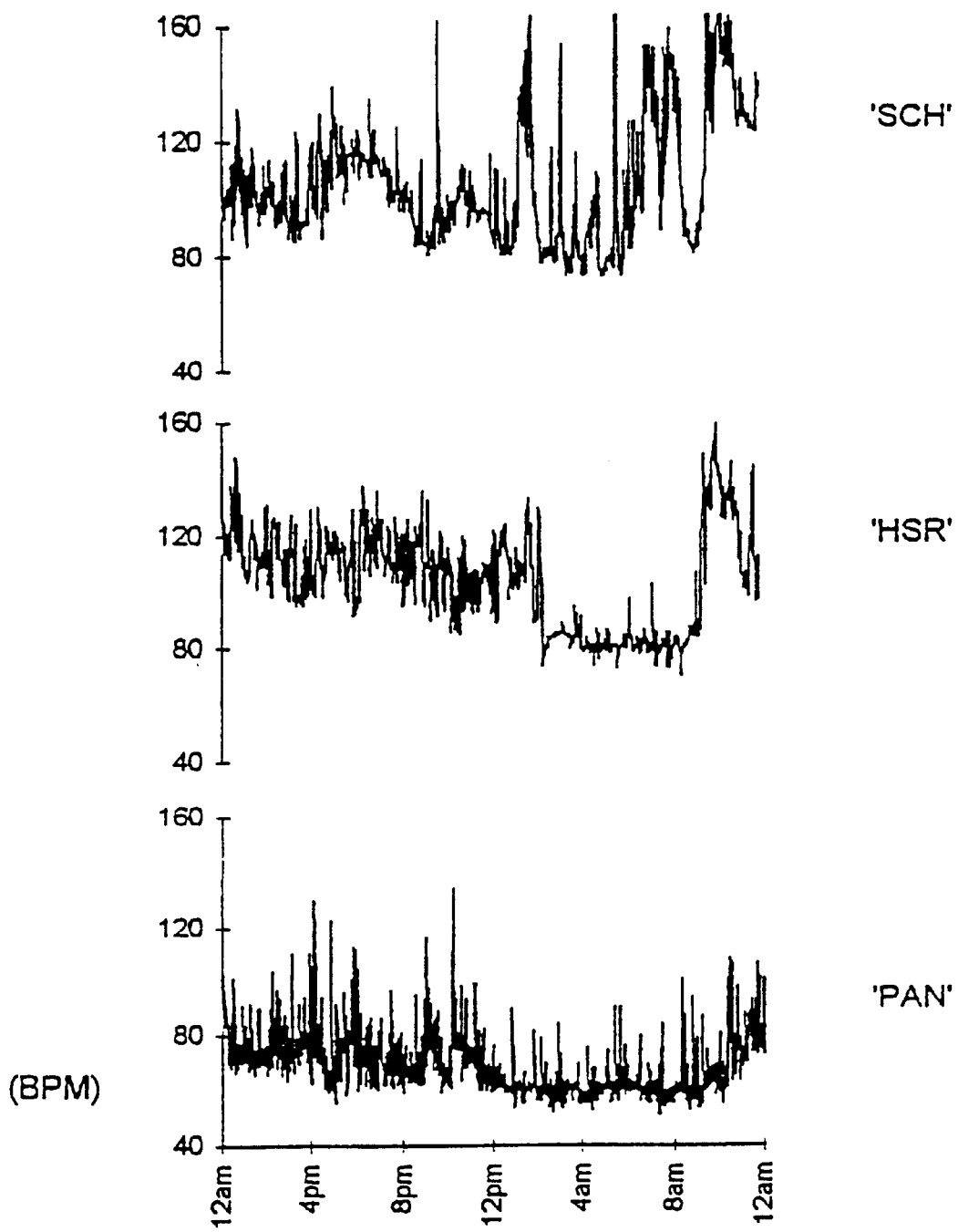
Figure 7:
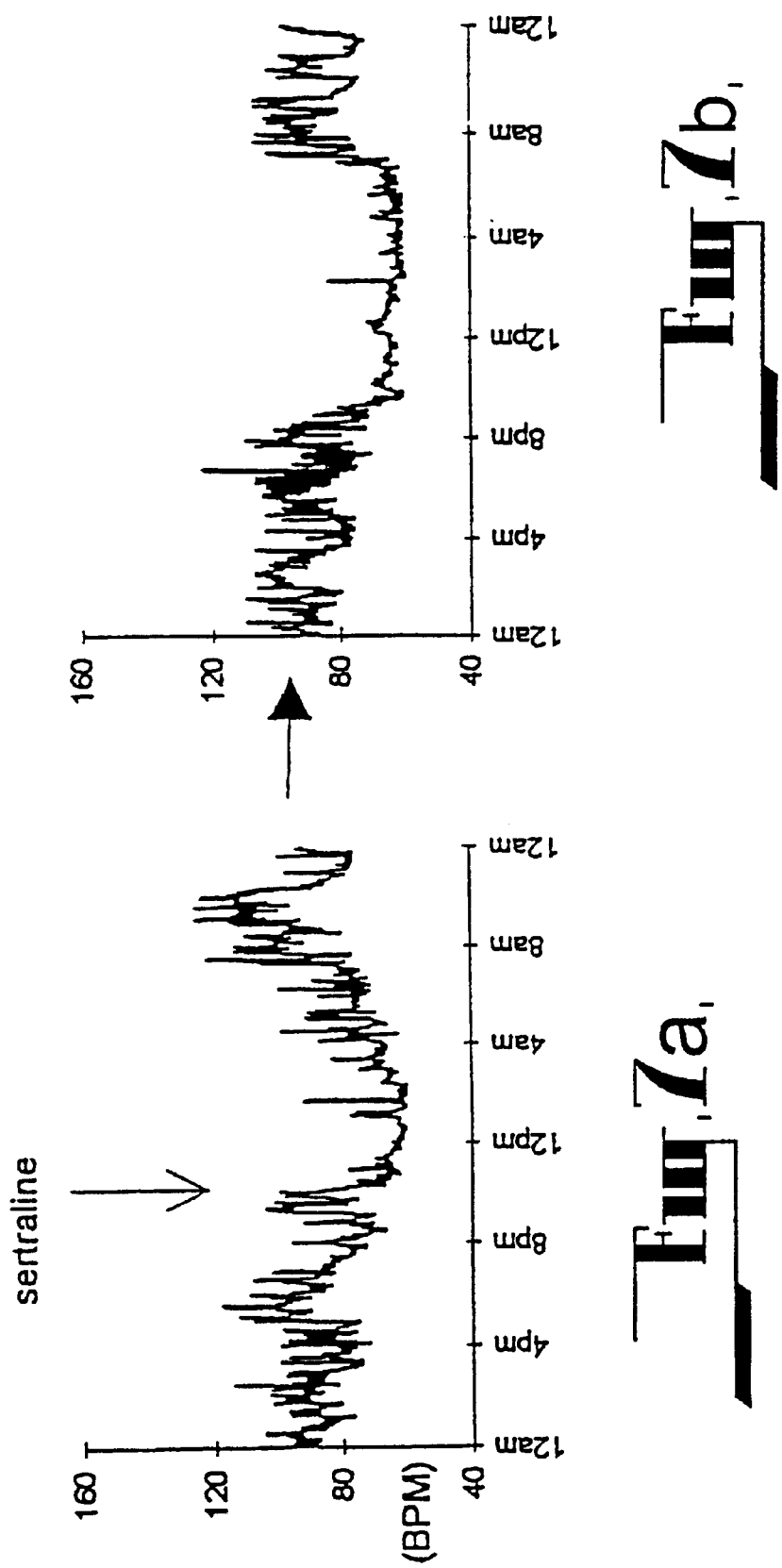

It appears that only when benzodiazepines have been effective in the treatment of generalized anxiety, do the broad contours of activity alter significantly (as illustrated in FIG. 4). In contrast to benzodiazepines, anti-depressants (including SSRI's TCA's and RIMA's) do not show any visibly obvious transient effects, but can lead to more profound changes when clinically effective. This is illustrated in FIGS. 7a and 7b which show significant changes in a DEP pattern, after three weeks treatment with Sertraline and undoubted clinical improvement. A comparison of FIGS. 7a and 7b shows that the presumed effect of treatment with sertraline, has been to normalize the circadian pattern to here the sleep period resembles the pattern seen in normal subjects and there has been a general reduction in the amount of minute pulse variation over much of the 24 hour period.

The examples demonstrate that there are qualitatively different patterns of circadian heart rate which cannot be reduced to mere quantitative variation in the 24 hour mean. Evidence has been presented to show that the qualitative aspect depends importantly on mental or psychiatric status and the predominance of particular patterns in broadly different diagnoses, suggests that the circadian pattern is an indication of broad physiological differences between these psychiatric states. Whilst some states show a strong association with a particular pattern, in others the pattern is more variable.

Conversely, given a recording which shows a particular pattern, (eg GAD), the clinical phenomena may vary from generalized anxiety, Panic Disorder, hypochondriacal Somatoform Disorder and even normal subjects may show such pattern. It is likely, that broadly different circadian patterns, which reflect broadly different states of physiological activation, can be associated with different mental state phenomena and it is in this sense that these data can contribute a physiological dimension to clinical assessment.

Thus, the information provided by these data, contribute significantly to the selection of more effective medication, the evaluation of treatment and the selection of more homogeneous populations in research.

Examples 1 and 2 show that changes in mental state are associated with variation in both the qualitative and quantitative aspects of circadian activity, such that serial recordings can provide practically useful indices of clinical change. Patients can serve as their own control and the changes in serial recordings provide more reliable indices of clinical change than those obtained with subjective rating scales.

Example 3

24 hour heart rate was converted into a complex analytical signal from which the instantaneous frequency is calculated. This example involves the study of the distribution of 'instantaneous frequency' over 24 hours in different disorders and shows clear quantifiable differences between various disorders during the sleep period. This applies particularly to depression which can be diagnosed very reliably with the measures obtained from this method of analysis.

Analysis is focused on ULTRADIAN rhythm [cycle less than 24 hours or 'circadian'] modulation of the signal's instantaneous frequency. The most discriminatory differences are evident at cycles of around 90 minutes. This is illustrated below in FIGS. 8 and 9.

Figure 9:
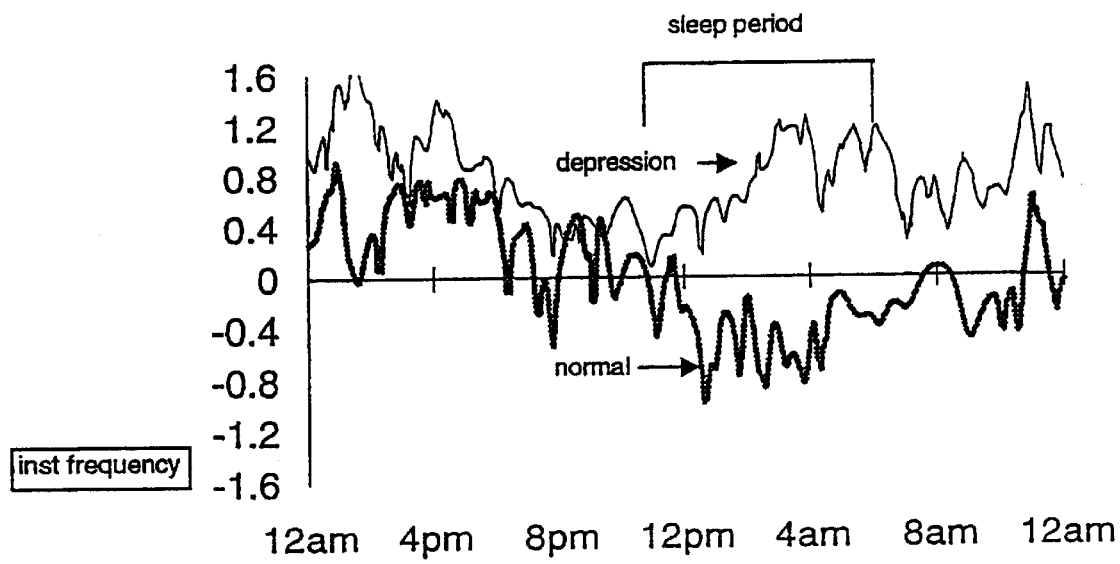

FIG. 8 shows individual examples and FIG. 9 shows group data comparisons between normal, anxiety and depression.

FIG. 8 in each plot pair, instantaneous frequency is shown on top, heart rate on the bottom the horizontal lines going through the circles indicate the 24 hour mean frequency.

the circles emphasise activity during the sleep period.

the arrows are located at the onset of sleep.

The bottom graph represents the profile of a normal subject. It can be seen that the instantaneous frequency in the normal subject shows a clear decline at the onset of sleep and is then modulated by phase stable 90 minute activity, which ceases its rhythmical fluctuations at the end of sleep.

The middle graph represents the profile of a subject suffering from anxiety. This too shows a fall around the onset of sleep but there is less phase stable modulation during sleep.

The upper graph represents the profile of a subject suffering from depression. There is a dramatic difference here in that the lowest most rhythmical rates occur before sleep and there is a dramatic rise in frequency from 3–4 pm. The second circle before the black arrow is intended to focus on the low frequency rhythmical activity which occurs before rather than after the onset of sleep as it does in the normal subject.

The group data contained in FIG. 9 shows differences in instantaneous frequency quite clearly and the prominent rise in frequency around 3 am in depression fits in well with a number of other findings of abnormal activity around this time.

The present invention includes within its scope adaptations and modifications apparent to one skilled in the art.

What is claimed is:

1. A method for diagnosing a psychiatric disorder in a subject, the method comprising the steps of:

measuring a heart rate pattern of the subject; and using said pattern to diagnose the psychiatric disorder.

2. A method according to claim 1 wherein the heart rate pattern is a circadian heart rate pattern.

3. A method according to claim 2 wherein a portion of the circadian heart rate pattern is used to diagnose the psychiatric disorder.

4. A method according to claim 3 wherein the portion of the circadian heart rate pattern is measured over approximately 90 minutes.

5. A method according to claim 3 wherein the portion of the circadian heart rate pattern includes at least a portion of the heart rate pattern exhibited whilst the subject is asleep.

6. A method according to claim 3 wherein the portion of the circadian heart rate pattern includes the portion of the heart rate pattern exhibited during the transition of the subject into or out of sleep.

7. A method according to claim 2 wherein the entire circadian heart rate pattern is used to diagnose the psychiatric disorder.

8. A method according to claim 1 wherein the heart rate pattern is measured as beats per minute over time.

9. A method according to claim 1 wherein the heart rate pattern is measured as a difference plot which reflects variations or fluctuations in heart rate.

10. A method according to claim 9 wherein the difference plot is a plot of heart rate (t+1)−heart rate (t), where t is time in minutes, over time.

11. A method according to claim 1 wherein the heart rate pattern is measured in a plurality of formats and the plurality of formats are used together to diagnose the psychiatric disorder.

12. A method according to claim 11 wherein the plurality of formats is beats per minute over time and heart rate (t+1)−heart rate (t), where t is time in minutes, over time.

13. A method according to claim 1 wherein the heart rate pattern of the subject is compared with at least one reference heart rate pattern indicative of a psychiatric disorder.

14. A method according to claim 13 wherein the reference heart rate pattern is provided in a computerized database.

15. A method accordingly to claim 1 wherein the heart rate pattern of the subject is compared to a plurality of reference heart rate patterns indicative of a psychiatric disorder, and wherein said reference heart rate patterns are developed by collecting data from a sufficient number of patients with psychiatric disorders to determine a typical pattern.

16. A method according to claim 1 wherein the subject's heart rate is measured with a monitor that is unobtrusive and leaves the person freely ambulant.

17. A method according to claim 1 wherein the psychiatric disorder is selected from the group comprising: General Anxiety Disorder (GAD), Panic Disorder (PD), Obsessive-Compulsive Disorder (OCD), non-psychotic Major Depression, Somatoform Disorder (hypochondriacal type), Delusional Disorder (paranoid and somatic type), Attention Deficit Disorder (ADD), and acute Schizophreniform Disorder.

18. A method for diagnosing a psychiatric disorder in a subject, the method comprising the steps of:

measuring a heart rate pattern of the subject;

comparing said heart rate pattern of the subject with a record of the subject's activities; and comparing said heart rate pattern of the subject with at least one reference heart rate pattern indicative of a psychiatric disorder wherein the comparison of said heart rate pattern with said record of the subject's activities allows for the effects of noise in said heart rate pattern of the subject to be negated.

19. A method according to claim 18 wherein the record of the subject's activities comprises a daily diary that is completed by the subject when being subjected to the method.

20. A method for assessing the effectiveness of a treatment for a psychiatric disorder in a subject, the method comprising the steps of:

measuring a heart rate pattern of the subject before said treatment;

measuring a heart rate pattern of the subject during said treatment; and comparing said patterns for changes to determine the effectiveness of said treatment.

21. A method according to claim 20 wherein the subject heart rate pattern is measured before, during and after said treatment to assess the efficacy of the treatment.

22. A method according to claim 20 wherein the treatment is a drug treatment.

23. A method according to claim 22 wherein the drug treatment involves the administration of a drug selected from the group comprising:

benzodiazepines;

anti-depressants such as Selective Serotonin Reuptake Inhibiters (SSRIs);

Tri-cyclic Antidepressants (TCAs);

Reversible Inhibitor of Monoamines (RIMAs); and sertraline.

\* \* \* \* \*